(12) United States Patent
Dowling et al.

(10) Patent No.: US 11,298,517 B2
(45) Date of Patent: *Apr. 12, 2022

(54) ADVANCED FUNCTIONAL BIOCOMPATIBLE FOAM USED AS A HEMOSTATIC AGENT FOR NON-COMPRESSIBLE ACUTE WOUNDS

(71) Applicant: University of Maryland, College Park, College Park, MD (US)

(72) Inventors: Matthew Dowling, Washington, DC (US); Srinivasa R. Raghavan, Silver Spring, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/251,553

(22) Filed: Jan. 18, 2019

(65) Prior Publication Data

US 2019/0192839 A1     Jun. 27, 2019

Related U.S. Application Data

(63) Continuation of application No. 15/443,009, filed on Feb. 27, 2017, now abandoned, which is a continuation of application No. 14/200,691, filed on Mar. 7, 2014, now abandoned, which is a continuation of application No. 12/946,818, filed on Nov. 15, 2010, now Pat. No. 8,668,899.

(60) Provisional application No. 61/261,194, filed on Nov. 13, 2009.

(51) Int. Cl.
*A61M 35/00*     (2006.01)
*A61L 26/00*     (2006.01)
*A61L 24/00*     (2006.01)

(52) U.S. Cl.
CPC ....... *A61M 35/003* (2013.01); *A61L 24/0026* (2013.01); *A61L 26/0076* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 4,394,373 A | 7/1983 | Malette et al. | |
| 4,532,134 A | 7/1985 | Malette et al. | |
| 4,572,906 A | 2/1986 | Sparkes et al. | |
| 4,645,757 A * | 2/1987 | Hjerten | A61K 9/146 514/54 |
| 4,752,466 A * | 6/1988 | Saferstein | A61K 9/12 424/45 |
| 4,895,724 A | 1/1990 | Cardinal et al. | |
| 5,243,094 A | 9/1993 | Borg | |
| 5,426,182 A | 6/1995 | Jenkins et al. | |
| 5,623,064 A | 4/1997 | Vournakis et al. | |
| 5,624,679 A | 4/1997 | Vournakis et al. | |
| 5,836,970 A | 11/1998 | Pandit | |
| 5,900,479 A | 5/1999 | Glasser et al. | |
| 5,919,574 A | 7/1999 | Hoagland | |
| 6,140,089 A | 10/2000 | Aebischer et al. | |
| 6,162,241 A | 12/2000 | Coury et al. | |
| 6,200,595 B1 | 3/2001 | Motoyashiki et al. | |
| 6,344,488 B1 | 2/2002 | Chenite et al. | |
| 6,371,975 B2 | 4/2002 | Cruise et al. | |
| 6,447,802 B2 | 9/2002 | Sessions et al. | |
| 6,458,147 B1 | 10/2002 | Cruise et al. | |
| 6,536,448 B2 | 3/2003 | McDevitt et al. | |
| 6,548,081 B2 | 4/2003 | Sadozai et al. | |
| 6,602,952 B1 | 8/2003 | Bentley et al. | |
| 6,663,653 B2 | 12/2003 | Akerfeldt | |
| 6,706,690 B2 | 3/2004 | Reich et al. | |
| 6,806,260 B1 | 10/2004 | Hirofumi et al. | |
| 6,827,727 B2 | 12/2004 | Stalemark et al. | |
| 6,830,756 B2 | 12/2004 | Hnojewyj | |
| 6,864,245 B2 | 3/2005 | Vournakis et al. | |

(Continued)

FOREIGN PATENT DOCUMENTS

| | | |
|---|---|---|
| EP | 927053 | 4/2003 |
| EP | 1115747 | 2/2004 |

(Continued)

OTHER PUBLICATIONS

Coster (Bag-On-Valve, 2007 (Year: 2007).*
Paul (Chitosan and Alginate Wound Dressings: A Short Review, 2004). (Year: 2004).*
Zhu et al., Reversible Vesicle Restraint in Response to Spatiotemporally Controlled Electrical Signals: A Bridge between Electrical and Chemical Signaling Modes, Langmuir 23(1) 286-291 (2007).
Whang, Hyun Suk et al., Hemostatic Agents Derived from Chitin and Chitosan, J. Macromolecular Science 45:309-323 (2005).
Wu et al., Spatially Selective Deposition of a Reactive Polysaccharide Layer onto a Patterned Template, Langmuir 19(3):519-524 (2003).
Wu et al., Voltage-Dependent Assembly of the Polysaccharide Chitosan onto an Electrode Surface, Langmuir 18(22):8620-8625 (2002).

(Continued)

*Primary Examiner* — Nghi V Nguyen
(74) *Attorney, Agent, or Firm* — The Morales Law Firm; Joseph L. Morales

(57) ABSTRACT

A sprayable polymeric foam hemostat for both compressible and non-compressible (intracavitary) acute wounds is disclosed. The foam comprises hydrophobically-modified polymers, such as hm-chitosan, or other amphiphilic polymers that anchor themselves within the membrane of cells in the vicinity of the wound. By rapidly expanding upon being released from a canister pressurized with liquefied gas propellant, the foam is able to enter injured body cavities and staunch bleeding. The seal created is strong enough to substantially prevent the loss of blood from these cavities. Hydrophobically-modified polymers inherently prevent microbial infections and are suitable for oxygen transfer required during normal wound metabolism. The amphiphilic polymers form solid gel networks with blood cells to create a physical clotting mechanism that prevent loss of blood.

8 Claims, 11 Drawing Sheets

(56) References Cited

U.S. PATENT DOCUMENTS

| | | | |
|---|---|---|---|
| 6,890,344 B2 | 5/2005 | Levinson | |
| 6,899,889 B1 | 5/2005 | Hnojewyj et al. | |
| 6,949,114 B2 | 5/2005 | Hnojewyj et al. | |
| 6,958,325 B2 | 10/2005 | Domb | |
| 6,967,261 B1 | 11/2005 | Soerens et al. | |
| 6,994,686 B2 | 2/2006 | Cruise et al. | |
| 6,995,137 B2 | 2/2006 | You et al. | |
| 7,019,191 B2 | 3/2006 | Looney et al. | |
| 7,041,657 B2 | 5/2006 | Vournakis et al. | |
| 7,098,194 B2 | 8/2006 | Chenite et al. | |
| 7,115,588 B2 | 10/2006 | Vournakis et al. | |
| 7,247,314 B2 | 7/2007 | Hnojewyj et al. | |
| 7,279,001 B2 | 10/2007 | Addis et al. | |
| 7,288,532 B1 | 10/2007 | Payne et al. | |
| 7,318,933 B2 | 1/2008 | Hnojewyj | |
| 7,320,962 B2 | 1/2008 | Reich et al. | |
| 7,351,249 B2 | 4/2008 | Hnojewyj et al. | |
| 7,371,403 B2 | 5/2008 | McCarthy et al. | |
| 7,482,503 B2 | 1/2009 | Gregory et al. | |
| 7,514,249 B2 | 4/2009 | Gower et al. | |
| 7,820,872 B2 | 10/2010 | Gregory et al. | |
| 7,897,832 B2 | 3/2011 | McAdams et al. | |
| 7,981,872 B2 | 7/2011 | Hardy et al. | |
| 8,088,095 B2 | 1/2012 | Hissong et al. | |
| 8,106,030 B2 | 1/2012 | Hardy et al. | |
| 8,119,780 B2 | 2/2012 | Baker et al. | |
| 8,152,750 B2 | 4/2012 | Vournakis et al. | |
| 8,269,058 B2 | 9/2012 | McCarthy et al. | |
| 8,361,504 B2 | 1/2013 | Hen et al. | |
| 8,382,794 B2 | 2/2013 | Belhe et al. | |
| 8,414,925 B2 | 4/2013 | Freier | |
| 8,481,512 B2 | 7/2013 | Vournakis et al. | |
| 8,486,033 B2 | 7/2013 | Orgill et al. | |
| 8,530,632 B2 | 9/2013 | Tijsma et al. | |
| 8,535,477 B2 | 9/2013 | Ladet et al. | |
| 8,536,230 B2 | 9/2013 | Laurencin et al. | |
| 8,623,274 B2 | 1/2014 | Kirsch et al. | |
| 8,653,319 B2 | 2/2014 | Amery et al. | |
| 8,658,193 B2 | 2/2014 | Greenwald | |
| 8,658,775 B2 | 2/2014 | Baker et al. | |
| 8,664,199 B2 | 3/2014 | Dowling et al. | |
| 8,668,899 B2 | 3/2014 | Dowling et al. | |
| 8,668,924 B2 | 3/2014 | McCarthy et al. | |
| 8,703,170 B2 | 4/2014 | Hedrich et al. | |
| 8,703,176 B2 | 4/2014 | Zhu et al. | |
| 8,715,719 B2 | 5/2014 | Roorda et al. | |
| 8,735,571 B2 | 5/2014 | DeCarlo et al. | |
| 8,741,335 B2* | 6/2014 | McCarthy | A61L 26/0023 424/445 |
| 8,771,258 B2 | 7/2014 | Hedrich et al. | |
| 8,795,727 B2 | 8/2014 | Gong et al. | |
| 8,802,652 B2 | 8/2014 | Myntti et al. | |
| 8,809,301 B2 | 8/2014 | Athanasiadis et al. | |
| 8,828,050 B2 | 9/2014 | Gregory et al. | |
| 8,835,528 B2 | 9/2014 | Pravata | |
| 8,840,867 B2 | 9/2014 | Lerouge et al. | |
| 8,920,514 B2 | 12/2014 | Gregory et al. | |
| 8,932,560 B2 | 1/2015 | Dowling et al. | |
| 8,951,565 B2 | 2/2015 | McCarthy | |
| 8,975,387 B1 | 3/2015 | Venditti et al. | |
| 8,993,540 B2 | 3/2015 | Haggard et al. | |
| 9,004,918 B2 | 4/2015 | McAdams et al. | |
| 9,012,429 B2 | 4/2015 | Baker et al. | |
| 9,029,351 B2 | 5/2015 | Baker et al. | |
| 9,034,379 B2 | 5/2015 | Freier | |
| 9,044,488 B2 | 6/2015 | Subramaniam et al. | |
| 9,061,087 B2 | 6/2015 | Roberts et al. | |
| 9,066,885 B2 | 6/2015 | Raghavan et al. | |
| 9,114,172 B2 | 8/2015 | Rhee et al. | |
| 9,119,894 B2 | 9/2015 | Huang et al. | |
| 9,132,206 B2 | 9/2015 | McCarthy | |
| 9,139,664 B2 | 9/2015 | Finkielsztein et al. | |
| 9,192,574 B2 | 11/2015 | Medina et al. | |
| 9,198,997 B2 | 12/2015 | Myntti et al. | |
| 9,205,170 B2 | 12/2015 | Lucchesi et al. | |
| 9,226,988 B2 | 1/2016 | Kirsch et al. | |
| 9,259,357 B2 | 2/2016 | Kirsch et al. | |
| 9,333,220 B2 | 5/2016 | Tijsma et al. | |
| 9,364,578 B2 | 6/2016 | Zhu et al. | |
| 9,370,451 B2 | 6/2016 | Hardy et al. | |
| 9,375,505 B2 | 6/2016 | Hedrich et al. | |
| 9,616,088 B2 | 4/2017 | Diehn et al. | |
| 2002/0028181 A1 | 3/2002 | Miller et al. | |
| 2002/0068151 A1 | 6/2002 | Kim et al. | |
| 2004/0001893 A1 | 1/2004 | Stupp | |
| 2005/0038369 A1 | 2/2005 | Gregory et al. | |
| 2005/0147656 A1 | 7/2005 | McCarthy | |
| 2005/0181027 A1 | 8/2005 | Messinger | |
| 2006/0094060 A1 | 5/2006 | Jarhede et al. | |
| 2006/0167116 A1 | 7/2006 | Uchegbu et al. | |
| 2006/0269485 A1* | 11/2006 | Friedman | A61K 9/107 424/45 |
| 2007/0055364 A1 | 3/2007 | Hossainy | |
| 2007/0148215 A1 | 6/2007 | Teslenko et al. | |
| 2008/0103228 A1 | 5/2008 | Falcone et al. | |
| 2008/0138296 A1* | 6/2008 | Tamarkin | A61K 8/375 424/47 |
| 2008/0254104 A1* | 10/2008 | Raghavan | A61K 47/69 424/445 |
| 2009/0062849 A1 | 3/2009 | Dowling | |
| 2009/0192429 A1 | 7/2009 | Daniels et al. | |
| 2009/0226391 A1 | 9/2009 | Roberts et al. | |
| 2010/0256671 A1* | 10/2010 | Falus | A61L 24/0031 606/214 |
| 2011/0052665 A1 | 3/2011 | Hardy et al. | |
| 2011/0217785 A1 | 9/2011 | Liu et al. | |
| 2012/0058970 A1 | 3/2012 | Dowling | |
| 2012/0252703 A1 | 10/2012 | Dowling | |
| 2014/0275291 A1 | 9/2014 | McGrath et al. | |
| 2015/0175714 A1 | 6/2015 | Dowling et al. | |
| 2015/0175718 A1 | 6/2015 | Dowling et al. | |
| 2016/0213704 A1 | 7/2016 | Dowling et al. | |
| 2017/0326169 A1 | 11/2017 | Dowling et al. | |
| 2017/0326171 A1 | 11/2017 | Dowling et al. | |

FOREIGN PATENT DOCUMENTS

| | | | |
|---|---|---|---|
| EP | 1294414 | 3/2006 | |
| EP | 1859816 | 9/2010 | |
| EP | 1401352 | 3/2012 | |
| EP | 2288744 | 7/2012 | |
| EP | 2358412 | 7/2012 | |
| EP | 2296637 | 4/2014 | |
| EP | 2340002 | 3/2015 | |
| EP | 2632502 | 5/2015 | |
| EP | 2473203 | 7/2016 | |
| WO | WO-2009037500 A1 * | 3/2009 | A61L 26/0066 |

OTHER PUBLICATIONS

Yoshina-Ishii et al., Diffusive Dynamics of Vesicles Tethered to a Fluid Supported Bilayer by Single-Particle Tracking, Langmuir 22(13):5682-5689 (2006).

Zhang, Jing. Drug Delivery: Self-Assembled Nanoparticles based on Hydrophobically Modified chitosan as Carriers for Doxorubicin, Nanomedicine, Elsevier. Aug. 2007. pp. 258-265.

Zhdanov et al. Adsorption and Spontaneous Rupture of Vesicles Composed of Two Types of Lipids (Langmuir 2006, 22, 3477-3480).

Zhdanov et al., Comments on Rupture of Adsorbed Vesicles (Langmuir 2001, 17, 3518-3521).

Zhu et al., Bioinspired Vesicle Restraint and Mobilization Using a Biopolymer Scaffold, Langmuir 22(7):2951-2955 (2006).

"The Hemostatic HemConA® Bandage." http://www.hemcon.com/ProductsTechnology/HemConBandageOverview.aspx.

Alam, Hasan B., et al. Comparative Analysis of Hemostatic Agents in a Swine Model of Lethal Groin Injury, J. Trauma 54:1077-1082 (2003).

Allerbo et al., Simulation of lipid vesicle rupture induced by an adjacent supported lipid bilayer patch (Colloids and Surfaces B: Biointerfaces 2011, 82, 632-636).

(56) References Cited

OTHER PUBLICATIONS

Anderluh et al., Properties of Nonfused Liposomes Immobilized on an L1 Biacore Chip and Their Permeabilization by a Eukaryotic Pore forming Toxin, Anal. Biochem. 344:43-52 (2005).

Angelova, M. I.; Dimitrov, D. S. "Liposome electroformation." Faraday Discuss. 1986, 81, 303-306.

Ankit R. Patel and Curtis W. Frank, Quantitative Analysis of Tethered Vesicle Assemblies by Quartz Crystal Microbalance with Dissipation Monitoring: Binding Dynamics and Bound Water Content, Langmuir 22(18):7587-7599 (2006).

Arnaud, F.; Teranishi, K.; Tomori, T.; Carr, W.; McCarron, R. "Comparison of 10 hemostatic dressings in a groin puncture model in swine." J. Vascular Surg. 2009, 50, 632-639.

Kheirabadi, B. S.; Scherer, M. R.; Estep, J. S.; Dubick, M. A.; Holcomb, J. B. "Determination of Efficacy of New Hemostatic Dressings in a Model of Extremity Arterial Hemorrhage in Swine." J. Trauma 2009, 67, 450-460.

Bochicchio, G.; Kilbourne, M.; Kuehn, R.; Keledjian, K.; Hess, J.; Scalea, T. "Use of a modified chitosan dressing in a hypothermic coagulopathic grade V liver injury model." Am. J. Surg. 2009, 198, 617-622.

Boukobza et al., Immobilization in Surface-Tethered Lipid Vesicles as a New Tool for Single Biomolecule Spectroscopy, J. Phys. Chem. B 105(48):12165-12170 (2001).

Brandenberg, Greg et al. Chitosan: A New Tropical Hemostatic Agent for Diffuse Capillary Bleeding in Brain Tissue, Neurosurgery 15(1): 9-13 (1984).

Burkatovskaya, Marina et al., Use of Chitosan Bandage to Prevent Fatal Infections Developing From Highly Contaminated Wounds in Mice, Biomaterials 27:4157-4164 (2006).

Champion, H. R.; Bellamy, R. F.; Roberts, C. P.; Leppaniemi, A. "A profile of combat injury." J. Trauma2003, 54, S13-S19.

Christensen, S. M.; Stamou, D. "Surface-based lipid vesicle reactor systems: fabrication and applications." Soft Matter 2007, 3, 828-836.

Chenite, A. et al "Rheological characterization of thermogelling chitosan/glycerol-phosphate solutions" Carbohydrate Polymers 46, 39-47 (2001).

Chiaki Yoshina-Ishii and Steven G. Boxer, Arrays of Mobile Tethered Vesicles on Supported Lipid Bilayers, J. Am. Chem. Soc. 125(13):3696-3697 (2003).

Kheirabadi, Bijan S. et al., Hemostatic Efficacy of Two Advanced Dressings in an Aortic Hemorrhage Model in Swine, J. Trauma Injury, Infection, and Critical Care, 59:25-35 (2005).

Cooper et al., A Vesicle Capture Sensor Chip for Kinetic Analysis of Interactions with Membrane-Bound Receptors, Anal. Biochem. 277:196-205 (2000).

Coster, Bag-On-Valve Series Offers Faster Filling and Better Drop Resistance. 2007. Downloaded from the world wide web on Jan. 18, 2012 <http://www.coster.com/news/eng/2007-10-18_AE_bov/AE_Manchester_BOV_eng.pdf.>.

D. D. Lasic and D. Papahadjopoulos, Liposomes Revisited, Science 267(5202):1275-1276 (1995).

Dan D. Lasic, Novel Applications of Liposomes, Trens in Biotechnology (TIBTECH) 16:307-321 (1998).

Deng, Y.; Wang, Y.; Holtz, B.; Li, J. Y.; Traaseth, N.; Veglia, G.; Stottrup, B. J.; Elde, R.; Pei, D. Q.; Guo, A.; Zhu, X. Y. "Fluidic and air-stable supported lipid bilayer and cell-mimicking microarrays." J. Am. Chem. Soc.2008, 130, 6267-6271.

Desbrieres et al., Hydrophobic Derivatives of Chitosan: Characterization and Rheological Behaviour, Biological Macromolecules, 19:21-28 (1996).

Dimitrievski et al., Influence of Lipid-Bilayer-Associated Molecules on Lipid-Vesicle Adsorption (Langmuir 2010, 26(8), 5706-5714).

Dimitrievski et al., Simujlations of Lipid Vesicle Adsorption for Different Lipid mixtures (Langmuir 2008, 24, 4077-4091).

Doolittle, R. F. "Fibrinogen and fibrin." Annu. Rev. Biochem. 1984, 53, 195-229.

Dowling, M.B., et al. "A self-assembling hydrophobically modified chitosan capable of reversible hemostatic action." Biomaterials. (May 2011) Vo. 31, pp. 3351-3357.

Durian, Douglas J., et al. "Making a frothy shampoo or beer." Physics Today. pp. 62-63. May 2010.

Eldin, Mohy et al. Chitosan Modified Membranes for Wound Dressing Applications: Preparations, Characterization and Bio-Evaluation. Trend Biomater. Atif.Organs. vol. 22 (3). pp. 158-168.

Ellis-Behnke, R. G.; Liang, Y. X.; You, S. W.; Tay, D. K. C.; Zhang, S. G.; So, K. F.; Schneider, G. E. "Nano neuro knitting: Peptide nanofiber scaffold for brain repair and axon regeneration with functional return of vision." Proc. Natl. Acad. Sci. U. S. A. 2006, 103, 5054-5059.

Ellis-Behnke, R. G.; Liang, Y.-X.; Tay, D. K. C.; Kau, P. W. F.; Schneider, G. E.; Zhang, S.; Wu, W.; So, K.-F. "Nano hemostat solution: Immediate hemostasis at the nanoscale." Nanomedicine 2006, 2, 207-215.

Esquenet et al.,Structural and Rheological Properties of Hydrophobically Modified Polysaccharide Associative Networks, Langmuir 20(9):3583-3592 (2004).

F W Verheugt, M J van Eenige, J C Res, M L Simoons, P W Serruys, F Vermeer, D C van Hoogenhuyze, P J Remme, C de Zwaan, and F Baer. Bleeding complications of intracoronary fibrinolytic therapy in acute myocardial infarction. Assessment of risk in a randomised trial.

Fernandes et al., Electrochemically Induced Deposition of a Polysaccharide Hydrogel onto a Patterned Surface, Langmuir 19(10):4058-4062 (2003).

Fu et al., Protein stability in controlled-release systems, Nature Biotechnology 18:24-25 (2000).

GlaxoSmithKline. Bactroban Ointment: Prescribing Information. Research Triangle Park, NC, May 2005. Downloaded from the world wide web on Jan. 17, 2013 <https://www.gsksource.com/gskprm/htdocs/documents/BACTROAN-OINTMENTS.PDF>.

Gregory F. Payne and Srinivasa R. Raghavan, Chitosan: a Soft Interconnect for Hierarchical Assembly of Nano-scale Components, Soft Matter 3:521-527 (2007).

Kurth, Dirk G. and Thomas Bein. "Monomolecular Layers and Thin Films of Silane Coupling Agents by Vapor-Phase Adsorption on Oxidized Aluminum." J. Phys. Chem. 1992. 96. 6707-6712.

Hirano and Noishiki, The Blood Compatibility of Chitosan and N-Acylchitosans, J. Biochem. Materials Res. 413-417 (1985).

Hou, et al. "Preparation and characterization of RGD-immobilized chitosan scaffolds," Biomaterials 26 (2005) 3197-3206, published Oct. 14, 2004.

Hong et al., Two-step Membrane Binding by Equinatoxin II, a Pore-forming Toxin from the Sea Anemone, Involves an Exposed Aromatic Cluster and a Flexible Helix, J. Biol. Chem. 277(44):41916-41924 (2002).

Hook et al., Supported Lipid Bilayers, Tethered Lipid Vesicles, and Vesicle Fusion Investigated Using Gravimetric, Plasmonic, and Microscopy Techniques, Biointerphases 3(2) (Jun. 2008).

Jung et al., Quantification of Tight Binding to Surface-Immobilized Phospholipid Vesicles Using Surface Plasmon Resonance: Binding Constant of Phospholipase A2, J. Am. Chem. Soc. 122(17):4177-4184 (2000).

Kaler et al., Phase Behavior and Structures of Mixtures of Anionic and Cationic Surfactants, J. Phys. Chem. 96(16):6698-6707 (1992).

Kaler et al., Spontaneous Vesicle Formation in Aqueous Mixtures of Single-Tailed Surfactants, Science 245(4924):1371-1374 (1989).

Kauvar, D. S.; Lefering, R.; Wade, C. E. "Impact of hemorrhage on trauma outcome: An overview of epidemiology, clinical presentations, and therapeutic considerations." J. Trauma 2006, 60, S3-S9.

Kean, T.; Thanou, M. "Biodegradation, biodistribution and toxicity of chitosan." Adv. Drug Deliv. Rev. 2010,62, 3-11.

Khan et al., Mechanical, Bioadhesive Strength and Biological Evaluations of Chitosan Films for Wound Dressing, J. Pharm. Pharmaceut. Sci. 3(3):303-311 (2000).

Kim, Seung-Ho MD; Stezoski, S. William; Safar, Peter MD; Capone, Antonio MD; Tisherman, Samuel MD. "Hypothermia and Minimal Fluid Resuscitation Increase Survival after Uncontrolled Hemorrhagic Shock in Rats" Journal of Trauma-Injury Infection & Critical Care. 42(2):213-222, Feb. 1997.

(56) References Cited

OTHER PUBLICATIONS

Kjoniksen et al., Light Scattering Study of Semidilute Aqueous Systems of Chitosan and Hydrophobically Modified Chitosans, Macromolecules 31(23):8142-8148 (1998).
Knoll, W.; Frank, C. W.; Heibel, C.; Naumann, R.; Offenhausser, A.; Ruhe, J.; Schmidt, E. K.; Shen, W. W.; Sinner, A. "Functional tethered lipid bilayers." J. Biotechnol. 2000, 74, 137-58.
Koehler et al., Microstructure and Dynamics of Wormlike Micellar Solutions Formed by Mixing Cationic and Anionic Surfactants, J. Phys. Chem. B 104(47):11035-11044 (2000).
Yoshina-Ishii et al. "General Method for Modification of Liposomes for Encoded Assembly on Supported Bilayers." J. Am. Chem. Soc. 2005, 127, 1356-1357.
Kozen, Buddy G. et al., An Alternative Hemostatic Dressing: Comparison of CELOX, HemCon, and QuikClot, Acad Emerg. Med. 15:74-81(2008).
Kubota, et al. Gelation Dynamics and Gel Structure Fibrinogen, Colloids Surf. B. Biointerfaces 38:103-109 (2004).
Kumar, R.; Raghavan, S. R. "Thermothickening in solutions of telechelic associating polymers and cyclodextrins." Langmuir 2010, 26, 56-62.
Larson, M. J.; Bowersox, J. C.; Lim, R. C.; Hess, J. R. "Efficacy of a fibrin hemostatic bandage in controlling hemorrhage from experimental arterial injuries." Arch. Surg. 1995, 130, 420-422.
Lee et al., Transition from Unilamellar to Bilamellar Vesicles Induced by an Amphiphilic Biopolymer, Phys. Review Letters, 96:048102-1-048102-4 (2006).
Lee et al., Vesicle-Biopolymer Gels: Networks of Surfactant Vesicles Connected by Associating Biopolymers, Langmuir 21(1):26-33 (2005).
Lew, W. K.; Weaver, F. A. "Clinical use of topical thrombin as a surgical hemostat." Biologies 2008, 2, 593-599.
Li et al., Multivesicular Liposomes for Oral Delivery of Recombinant Human Epidermal Growth Factor, Arch Pharm Res 28(8):988-994 (2005).
Lu, S. et al. "Preparation of Water-Soluble Chitosan" Journal of Applied Polymer Science 91, 3497-2503 (2004).
Lunelli et al., Covalently Anchored Lipid Structures on Amine-Enriched Polystyrene, Langmuir 21(18):8338-8343 (2005).
Macfarlane, R. G. "An enzyme cascade in the blood clotting mechanism, and its function as a biological amplifier." Nature 1964, 202, 498-499.
Malette, William G. et al. Chitosan: A New Hemostatic, The Annals of Thoracic Surgery 36(1):55-58 (1983).
Mansur Yalpani and Laurence D. Hall, Some Chemical and Analytical Aspects of Polysaccharide Modifications. Formation of Branched-Chain, Soluble Chitosan Derivatives, Macromolecules 17(3):272-281 (1984).
Mathivet et al., Shape Change and Physical Properties of Giant Phospholipid Vesicles Prepared in the Presence of an AC Electric Field, Biophysical Journal 70:1112-1121 (1996).
Meier, Wolfgang et al., Vesicle and Cell Networks: Interconnecting Cells By Synthetic Polymers, Langmuir 12:5028-5032 (1996).
Michael I. Fisher and Torbjorn Tjarnhage, Structure and Activity of Lipid Membrane Biosensor Surfaces Studied with Atomic Force Microscopy and a Resonant Mirror, Biosensors & Bioelectronics 15:463-471 (2000).
Naumann et al., Proton Transport Through a Peptide-tethered Pilayer Lipid Membrane by the H+-ATP Synthase from Chloroplasts Measured by Impedance Spectroscopy, Biosensors and Bioelectronics 17:25-34 (2002).
Naumann, C. A.; Prucker, O.; Lehmann, T.; Ruhe, J.; Knoll, W.; Frank, C. W. "The polymer-supported phospholipid bilayer: Tethering as a new approach to substrate-membrane stabilization." Biomacromolecules 2002, 3, 27-35.
Neuffer, M. C.; McDivitt, J.; Rose, D.; King, K.; Cloonan, C. C.; Vayer, J. S. "Hemostatic dressings for the first responder: A review." Military Med. 2004, 169, 716-720.

New ! Pioneer Chip L1 Improved binding studies in model membrane systems, BIA Journal No. 2 1998.
Nikolelis et al., A Minisensor for the Rapid Screening of Sucralose Based on Surface-stabilized Bilayer Lipid Membranes, Biosensors & Bioelectronics 15:439-444 (2000).
Paul S. Cremer and Steven G. Boxer, Formation and Spreading of Lipid Bilayers on Planar Glass Supports, J. Phys. Chem. B 103(13):2554-2559 (1999).
Pusateri, A. E.; Holcomb, J. B.; Kheirabadi, B. S.; Alam, H. B.; Wade, C. E.; Ryan, K. L. "Making sense of the preclinical literature on advanced hemostatic products." J. Trauma 2006, 60, 674-682.
Puu et al., Retained Activities of Some Membrane Proteins in Stable Lipid Bilayers on a Solid Support, Biosensors and Bioelectronics 10:463-476 (1995).
Raghavan, S. R.; Cipriano, B. H. Gel formation: Phase diagrams using tabletop rheology and calorimetry. In Molecular Gels; Weiss, R. G., Terech, P., Eds.; Springer: Dordrecht, 2005; pp. 233-244.
Rao, S. B.; Sharma, C. P. "Use of chitosan as a biomaterial: Studies on its safety and hemostatic potential." J. Biomed. Mater. Res. 1997, 34, 21-28.
Redepenning, J. et al. "Electrochemical preparation of chitosan/hydroxyapatite composite coatings on titanium substrates." Journal of Biomedical Materials Research. vol. 66A. pp. 411-416. 2003.
Reiss, R. F.; Oz, M. C. "Autologous fibrin glue: Production and clinical use." Transfusion Med. Rev. 1996, 10, 85-92.
Rodriguez, M.S., et al "Interaction between chitosan and oil under stomach and duodenal digestive chemical conditions" Biosci. Biotechnol. Biochem. 69 (11), 2057-2062 (2005).
Rongen et al., Liposomes and Immunoassays, J. Immunol. Methods 204:105-133 (1997).
Tonelli, A. E. "Nanostructuring and functionalizing polymers with cyclodextrins." Polymer 2008, 49, 1725-1736.
Stavroula Sofou and James L. Thomas, Stable Adhesion of Phospholipid Vesicles to Modified Gold Surfaces, Biosensors and Bioelectronics 18:445-455 (2003).
Stewart, R. M.; Myers, J. G.; Dent, D. L.; Ermis, P.; Gray, G. A.; Villarreal, R.; Blow, O.; Woods, B.; McFarland, M.; Garavaglia, J.; Root, H. D.; Pruitt, B. A. "Seven hundred fifty-three consecutive deaths in a level 1 trauma center: The argument for injury prevention." J. Trauma 2003, 54, 66-70.
Szejtli, J. "Introduction and general overview of cyclodextrin chemistry." Chem. Rev. 1998, 98, 1743-1753.
Szymanska et al., Fullerene Modified Supported Lipid Membrane as Sensitive Element of Sensor for Odorants, Biosensors & Bioelectronics 16:911-915 (2001).
Tanaka, M.; Sackmann, E. "Polymer-supported membranes as models of the cell surface." Nature 2005,437, 656-663.
Tangpasuthadol, Surface Modification of Chitosan Films. Effects of Hydrophobicity on Protein Adsorption, Carbohydrate Res. 338:937-942 (2003).
Tanweer A. Khan and Kok Khiang Peh, A Preliminary Investigation of Chitosan Film as Dressing for Punch Biopsy Wound in Rats, J. Pharm. Pharmaceut. Sci. 6(1):20-26 (2003).
U.S. Office Action issued in related U.S. Appl. No. 12/077,173 dated Nov. 8, 2010.
U.S. Office Action issued in related U.S. Appl. No. 12/077,173 dated Apr. 14, 2011.
U.S. Office Action issued in related U.S. Appl. No. 12/231,571 dated Mar. 5, 2012.
U.S. Office Action issued in related U.S. Appl. No. 12/946,818 dated Jan. 28, 2013.
U.S. Notice of Allowance issued in related U.S. Appl. No. 12/946,818 dated Oct. 29, 2013.
U.S. Office Action issued in related U.S. Appl. No. 13/209,399 dated Mar. 1, 2013.
U.S. Office Action issued in related U.S. Appl. No. 13/310,579 dated Apr. 11, 2013.

* cited by examiner (a) dodecyl aldehyde:

(b) 4-octadecyl aldehyde:

(c) cis-oleoyl chloride:

ADVANCED FUNCTIONAL BIOCOMPATIBLE FOAM USED AS A HEMOSTATIC AGENT FOR NON-COMPRESSIBLE ACUTE WOUNDS

CROSS REFERENCE TO RELATED APPLICATIONS

This application is a continuation of U.S. patent application Ser. No. 15/443,009 filed Feb. 27, 20017, which, in turn, claims priority from U.S. patent application Ser. No. 14/200,691 filed on Mar. 7, 2014, and U.S. patent application Ser. No. 12/946,818 filed Nov. 15, 2010, now U.S. Pat. No. 8,668,899 issued Mar. 11, 2014, which claims the priority benefit under 35 U.S.C. § 119(e) of U.S. Provisional Application No. 61/261,194, entitled "ADVANCED FUNCTIONAL BIOCOMPATIBLE FOAM USED AS A HEMOSTATIC AGENT FOR NON-COMPRESSIBLE ACUTE WOUNDS" filed Nov. 13, 2009, all above-referenced applications are incorporated herein by reference in their entirety.

BACKGROUND OF THE INVENTION

Field of the Invention

The present invention is generally related to the field of biopolymer applications for the treatment of wounds.

Background

The phrase the "Golden Hour" has been popularized to describe the first 60 minutes following a critical injury. Severe injuries are usually accompanied by hemorrhage, i.e., a copious loss of blood from the site of the wound. Effective control of hemorrhage within the "Golden Hour" can mean a difference between life and death. Hemorrhage is the greatest threat to survival in the first 24 hours after traumatic injury. It accounts for 39% of civilian trauma deaths, most of which occur before patients reach the hospital. In the battlefield too, severe injury accompanied by hemorrhage is a stark reality and is the leading cause of death to soldiers in combat. The majority of hemorrhagic deaths on the battlefield (approximately 90%) are due to intracavitary hemorrhage that is not accessible to direct pressure and cannot be controlled by these traditional methods. This has left first responders with no means to treat truncal (i.e. abdominal, thoracic, neck) hemorrhage other than fluid resuscitation. As a further damage, the administration of intravenous fluids, by diluting coagulation factors and platelets, tends to promote bleeding. Even for the few who make it to the operating room alive, patients with acute bleeding from truncal injuries can present significant challenges to surgeons who possess multiple surgical techniques, sophisticated equipment and a variety of hemostatic materials.

The past decade has seen enormous strides in acute wound care technology. Several materials have been well engineered to rapidly stop bleeding from severe injuries. Such technologies have been particularly useful to soldiers in combat. Key products contracted to the military include 1) Quickclot®, a zeolite powder which absorbs large amounts of water and hence concentrates clotting factors, 2) the Hemcon Bandage®, a freeze-dried bandage composed of chitosan, a material extracted from shrimp shells, and 3) Woundstat™, a clay mineral-based powder which, like Quickclot®, absorbs high volumes of fluid quickly. Additionally, there is a multitude of other products which attempt to achieve the same goals as the aforementioned products which have either passed FDA approval or are currently in development.

While these products typically do an adequate job of treating severe bleeding from extremities or superficial wounds, none of them are suited to treat non-compressible hemorrhage, i.e., injuries which are not accessible to direct pressure, usually at an intracavitary site (abdominal, thoracic, truncal). This is a very significant problem because the majority of deaths due to severe bleeding result from non-compressible hemorrhage. Surgery is unfortunately the only means available in the present day for treating non-compressible bleeding. Thus, development of more advanced technology to treat non-compressible wounds is a central issue in saving the lives of severe trauma victims.

Massive bleeding from internal organs, such as the liver or spleen, is currently controlled by mechanical surgical devices or packing of the wound with standard gauze. Both of these procedures can be performed on the operating table, but not on the battlefield or the site of an accident. While control of hemorrhage within the "Golden Hour" is key, all current methods and hemostatic agents for control of intracavitary hemorrhage are only useful within the context of a controlled environment with an open and/or injured body cavity under monitoring by medical professionals. Hence, hemostatic agents and delivery systems for these agents, which can be effectively applied by an unskilled "buddy" in the field to control massive intracavitary hemorrhage are in great need.

Biological glues which can adhere to tissues have also been used in intracavitary injuries. In general, synthetic adhesives are used for the tight sealing of vessels and sealing of skin incisions. These synthetics often contain cyanoacrylates, such as 2-butyl cyanoacrylate and 2-octyl cyanoacrylate. Unfortunately, such materials have unfavorable toxicity and biodegradation profiles and are difficult to remove without significant tissue damage.

The key products in high-tech hemostats for the emergency and critical care arena are Quickclot® (Z-Medica), a highly-absorbent zeolite powder, WoundStat™ (Traumacure), a highly-absorbent clay mineral powder, and the Hemcon® Bandage (Hemcon), which is made of chitosan, a natural biopolymer that sticks strongly to blood and fights infection. Despite their advancements over the perennially-used cotton gauze for combat settings, these products have not significantly decreased death from non-compressible hemorrhage injuries and they most likely will not. This is because they are either extremely difficult to resect/remove (Quickclot, Woundstat) without damaging tissue, or they don't adhere for a long enough time (Hemcon bandage). Both of these properties are very unfavorable for treating intracavitary bleeding. There are additional effective hemostatic products based on clotting biologic proteins such as fibrinogen and thrombrin, however they are extremely high cost, and no commercially available biologics have been shown to stop non-compressible bleeding

SUMMARY OF THE INVENTION

An apparatus for the treatment of wounds is described. In one embodiment of the present invention, an apparatus holds a multiple component composition in the liquid state. The composition is delivered via propellant onto wounded and/or bleeding tissue in vivo, where it then becomes elastic in character allowing for control of hemorrhage and tissue exudation. The apparatus comprises a valve system attached to a canister that contains a hydrophobically modified polymer, more specifically a hydrophobically modified polysaccharide, in a concentration of about 0.1% to about 2.0% by weight and a propellant. The hydrophobically modified polymer contained in the canister can be selected from the group consisting of hydrophobically modified chitosan, hydrophobically modified cellulosics, and hydrophobically modified alginates. If a hydrophobically modified chitosan is used, it can be selected from the group consisting of chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof. In one embodiment where a hydrophobically modified cellulosic is used, it can be selected from the group consisting of hydroxyetyhl cellulose, hydroxypropyl cellulose, methyl cellulose, hydroxypropyl methyl cellulose, hydroxyethyl methyl cellulose.

The mixture in the canister can have other elements in addition to the hydrophobically modified polymer. For example, the canister may contain a plasticizing agent such as glycerol, glycerophosphate, polyethylene glycol (PEG), polyethylene oxide (PEO), tripolyphosphate, polycaprolactone, polyurethane, and silicone. In one preferred embodiment, the canister may contain a mixture of hydrophobically-modified chitosan and glycerol in a ratio of 80:20 by weight and a propellant. The mixture in the canister can also contain other reagents that contribute to hemostatic integrity of a clot formed between the hydrophobically modified polysaccharide and blood cells and tissues in a wound. Some of such reagents may include human thrombin, bovine thrombin, recombinant thrombin, Factor VIIa, Factor XIII, and human fibrinogen. The mixture may further contain antimicrobial agents to aid in healing the wound.

In another embodiment of the present invention, a bag-on-valve system can be utilized in which the hydrophobically modified polysaccharide is in a bag inside the canister and a pressurized gas surrounds the bag. In this particular embodiment, the propellant does not mix directly with the hemostatic composition.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION OF THE INVENTION

Figure 1:
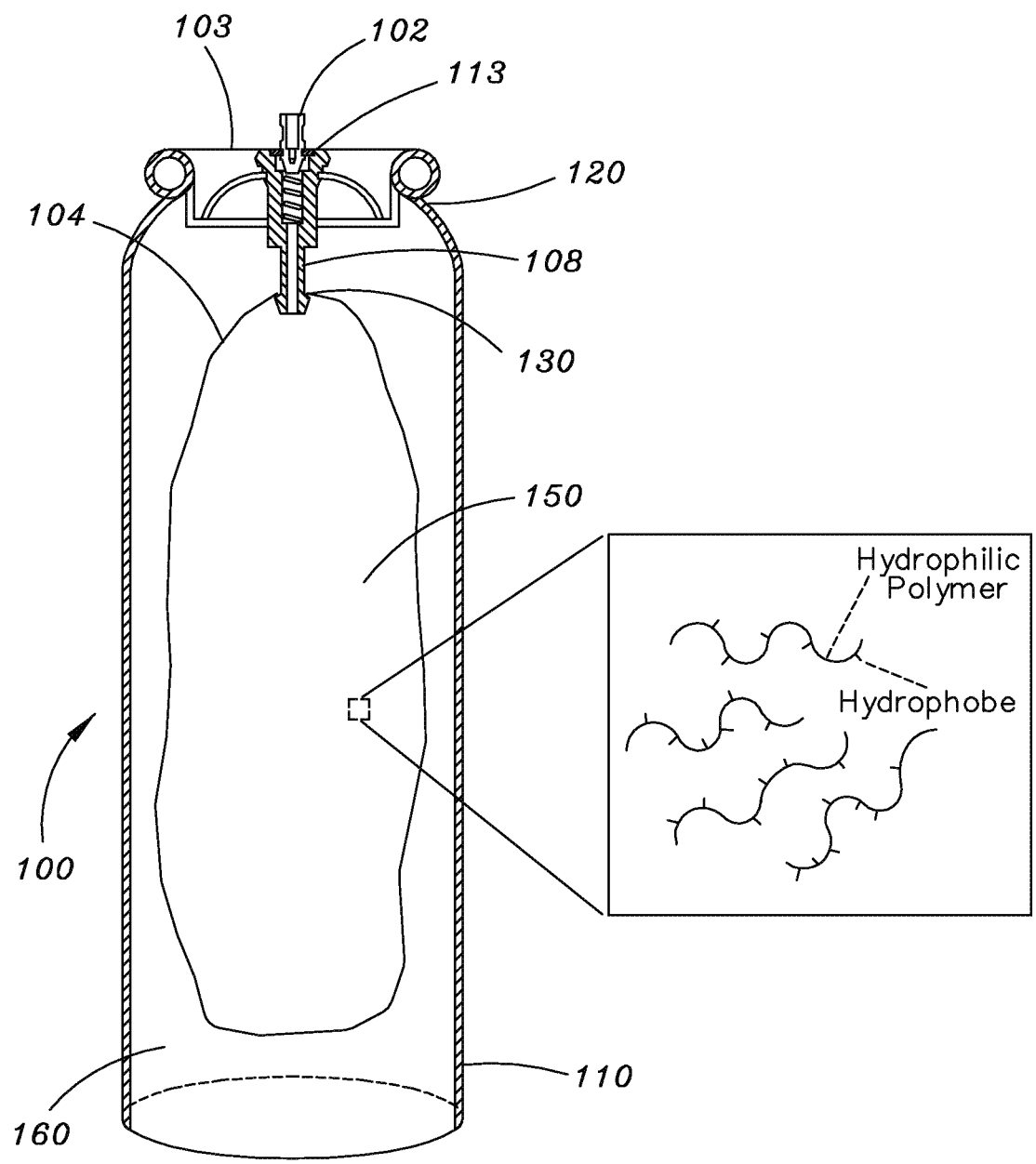
FIG. 1 is a schematic depiction of a bag-on-valve aerosol delivery apparatus in accordance with one embodiment of the present invention.

The invention summarized above may be better understood by referring to the following description, which should be read in conjunction with the accompanying claims and drawings in which like reference numbers are used for like parts. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent constructs and cell lines do not depart from the spirit and scope of the invention in its broadest form.

The present alternative approach is the development of an apparatus which contains and delivers a hemostatic composition on demand to the site of injury without any compression required. The hemostatic composition consists of hydrophilic polymers dissolved in water which have hydrophobes covalently attached along the polymer backbone. As a result of the amphiphilicity of these hydrophobically modified polymers, two important capabilities are present in the composition. Firstly, the composition of the amphiphilic polymer itself acts as a foaming agent. Much like popular surfactants, such as sodium lauryl sulfate or sodium oleate, which act as foaming agents due to their highly amphiphilic nature, these amphiphilic polymers too can act as adequate foaming agents. Hence, upon dispensation from a pressurized canister via gas or liquefied gas propellant, the amphiphilic polymer will foam and expand into oddly shaped injuries, whereas a non hydrophobically-modified counterpart will not foam. Secondly, the hydrophobes along the polymer backbone allow for rapid hemostasis. This occurs because the hydrophobes anchor themselves into the hydrophobic outer membranes of blood and soft tissue cells, thus creating a self-assembled 3-dimensional network which behaves as an elastic gel.

An apparatus for the delivery of a hemostat solution to a wound is described. A "hemostat" means a hydrophobically modified polysaccharide that adheres to tissues, forms clots with red blood cells and effectively stops hemorrhage. A "hemostatic composition" is a solution comprising a hemostat, which is delivered by the apparatus described in one embodiment of the present invention. "Hemostasis" is the point at which bleeding has stopped after treatment with a hemostat. The hemostat delivered by the apparatus described in one embodiment of the present invention can be utilized to treat compressible and non-compressible hemorrhages. Hemostats described in accordance with the present invention are amphiphilic polymers such as hydrophobically modified polysaccharides which are able to expand into an injured body cavity, adhering to tissue and stopping hemorrhage rapidly during the expansion process. The amphiphilic nature of the modified biopolymer promotes rapid clotting of blood as well as strong adhesion to tissue due to insertion of hydrophobes into blood and tissue cells, resulting in formation of a network which staunches bleeding. In one embodiment of the present invention, the hemostat is a hydrophobically modified chitosan, referred to throughout this application as hm-chitosan.

As shown in FIG. 1, in one embodiment of the present invention, the apparatus 100 comprises a canister 110 having a valve housing 113 attached to the canister 100. The canister 100 is a conventional cylindrical closed container. In some embodiments of the present invention, the canister 110 is made of aluminum, but other durable materials capable of holding liquids and gasses under pressure can also be utilized. In one preferred embodiment the canister 100 is 7 inches in height and 1.5 inches in diameter. The canister 100 has a top circular opening 120 within which is mounted an aerosol mounting cup 103. Centrally disposed within the mounting cup 103 is an aerosol valve 102 comprised of a valve stem 108 and a valve housing 113. A flexible bag 104 is attached to the lower end 130 of the valve stem 108 separating the hydrophobically modified polysaccharide 150 from a propellant contained in the propellant space 160.

The flexible bag 104 can be comprised of polyethylene and/or other materials (including in laminated form) and is of well known structure. The flexible bag 104 is a closed structure throughout except at the top of the flexible bag 104 where it is open only into the lower end 130 of the valve stem 108. The flexible bag 104 is welded along the circumference of its top opening to the outside of the lower end 130 of the valve stem 108. The flexible bag 104 extends down into the canister 110 to near the bottom of the canister 110. The valve stem 108 includes a central dispensing channel and lateral side orifices which are sealed by a gasket when the aerosol valve is closed by an annular gasket, which has a central opening. A spring in the interior of the valve housing biases the valve stem to a closed position when the valve is not actuated. The flexible bag 104 contains a hydrophobically modified polysaccharide 150 to be delivered to a wound through the valve stem 108.

The apparatus 100 is pressurized by a propellant in the propellant space 160. In one exemplary embodiment, Nitrogen may be used as the propellant and introduced at a pressure of 100 psig. When the valve stem 108 is depressed (or moved laterally in the case of tilt valve), the gasket unseals from the lateral stem orifices. The pressure of the propellant outside the bag presses inward against the flexible bag to force the hydrophobically modified polysaccharide, e.g., hm-chitosan, in the flexible bag 104 up through the interior of the valve housing 103, through lateral orifices and up the valve stem 108 of the dispensing channel to the outside environment. An actuator may be used to activate the valve stem 108 for dispensing the hydrophobically modified polysaccharide. When the valve stem 108 is no longer actuated, a spring forces the valve stem 108 back to its position where the gasket again seals lateral orifices to prevent further dispensing.

Figure 2:
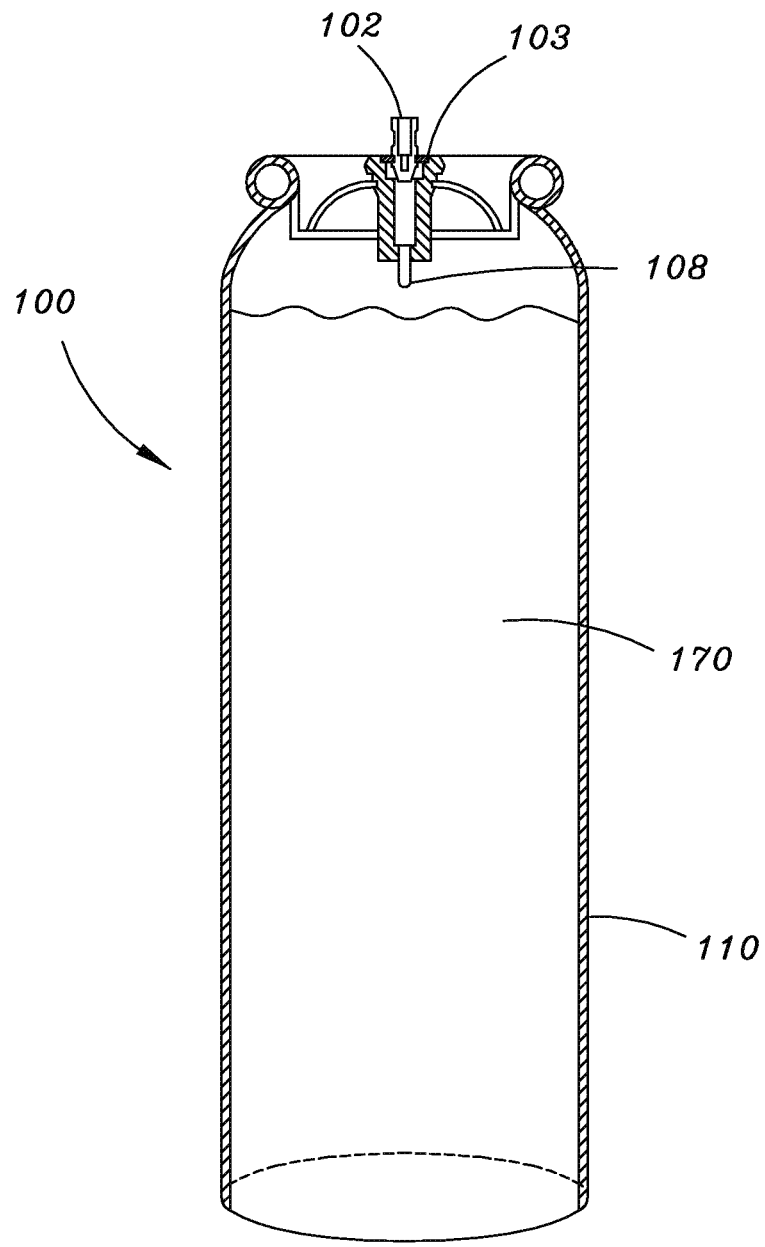
FIG. 2 is a schematic depiction of an open aerosol delivery apparatus in accordance with one embodiment of the present invention.

In a second preferred embodiment, as shown in FIG. 2, the apparatus 100 comprises a canister 110 and the valve housing 113. A valve stem 108 and valve housing 113 is crimped onto the top circular opening. The hydrophobically modified polysaccharide is mixed with a propellant to form a hemostat/propellant mixture 170. In one preferred embodiment, liquid hydrocarbon propellant A70 (70% propane, 30% isobutane) is backfilled through the valve via a standard pressurized filling line as is known to those skilled in the art. The propellant is added in a weight ratio of 9:1 (hydrophobically-modified chitosan: A70) up to a pressure of 100 psig. In this embodiment, the propellant is directly mixed with the hydrophobically modified polysaccharide, e.g., hm-chitosan, in a central canister chamber 180. A valve actuator is then added onto the valve stem 108 for dispensing. The pressure of the propellant forces the hemostat solution, e.g., hm-chitosan, in the canister chamber 180 through the interior of the valve housing, through the lateral orifices and up the stem of the dispensing channel to the outside environment. In one further preferred embodiment, the hydrophobically-modified polysaccharide, e.g., hm-chitosan, at a concentration of 1 wt % in 0.2 M Acetic Acid is poured into the open cylindrical aluminum canister and the propellant is backfilled through the valve as described above.

A hemostatic foam is created when the hydrophobically modified polysaccharide, e.g., hm-chitosan, composition is exposed to increased pressure in the presence of a charging gas. Charging gasses may include but are not limited to $CO_2$, $N_2$, a noble gas such as helium, neon, argon, hydrocarbon gases, such as isopentane, isobutane, butane, propane, or any other gas that is relatively inert physiologically and does not adversely affect the polymers, coagulants or any other component of the mixture. Upon releasing the pressure, such as by opening the valve, the pressure in the canister forces some of the gas/polymer mixture out of the canister, thereby relieving pressure on the polymer liquid. Some gas dissolved in the liquid comes out of solution and can form bubbles in the liquid, thereby forming the foam. The foam then expands until the gas pressure within the foam reaches equilibrium with the ambient pressure.

It is contemplated that various formulations can be used in order to deliver the hemostatic composition. In one exemplary embodiment, the hydrophobically-modified chitosan is mixed with glycerol at a weight ratio of 80:20 chitosan:glycerol, prior to addition into the bag-on-valve system pressurized by compressed nitrogen gas, as described above. In an alternative embodiment, the hydrophobically-modified chitosan is mixed with glycerol at a weight ratio of 80:20 chitosan:glycerol, prior to addition to a standard canister. Propellant A70 is then backfilled through the valve and mixed with the chitosan-glycerol mixture in the liquid state. In yet another exemplary embodiment, the hydrophobically modified polysaccharide is in a 1 wt % hm-chitosan solution.

In an embodiment, the hydrophobically modified polysaccharide is a sprayable biopolymer hemostat comprising at least one water-soluble polysaccharide and a plurality of short hydrophobic alkyl substituents attached along the backbone of the polysaccharide. The sprayable biopolymer foams once it is delivered by the apparatus. The foam is able to adhere strongly to tissue and clot blood due to anchoring of the hydrophobic grafts into the membranes of soft tissue cells and blood cells in the vicinity of the injury. As a result, the foam is an effective agent for stopping hemorrhage. The level of hydrophobic modification of the polysaccharide as well as hydrophobic substituent type is substantially optimized to develop foams which adhere to tissue in a manner idealized for clinical applications: the material comprising foam adheres strongly enough to provide hemostasis for a long enough time period to allow for substantially full patient recovery, yet weakly enough such that newly formed tissue is substantially undamaged upon removal of residual material after patient recovery. When a biocompatible and bioresorbable polysaccharide, such as chitosan, alginate, gellan gum or hyaluronic acid, is used, the foam can be left inside the patient as the material will naturally degrade into harmless monosaccharide substituents. Biocompatible plasticizing agents such as glycerol, glycerophosphate, polyethylene glycol (PEG), polyethylene oxide (PEO), tripolyphosphate, polycaprolactone, polyurethane, and silicone can be mixed with the polysaccharide formulation to improve its functionality. Plasticizing agents can be used to control adhesiveness, viscosity, bioreactivity, ability to expand, wound coverage ability, and wound healing capability.

The hydrophobically modified polysaccharide foam sprayed is able to form solid gel-like networks upon interaction with blood, as the hydrophobic substituents are able to anchor themselves within the bilayers of blood cell. The result is a localized "artificial clot" which physically prevents further blood loss around the newly formed solid network. "Artificial clots" herein refer to physical networks of hydrophobically modified polysaccharides, blood cells, and surround tissue cells which effectively act as a solid barrier to prevent further blood loss. Additionally, the level of hydrophobic modification of the polysaccharide as well as hydrophobic substituent type can be substantially optimized to yield rapidly forming and mechanically robust artificial clots. In an example, the hydrophobically modified polysaccharide foam is dispensed with at least one water-soluble reagent that results in faster and more efficient healing of the wound.

The polymeric components suitable for use in the sprayable foam hemostat can comprise one or more hydrophobically modified polysaccharides selected from the group consisting of cellulosics, chitosans and alginates. Such polysaccharides starting materials from which the hydrophobically modified polysaccharides can be made are known to those skilled in the art. Cellulosics, chitosans and alginates are all abundant, natural biopolymers. Cellulosics are found in plants, whereas chitosans and alginates are found in the exoskeleton or outer membrane of a variety of living organisms. All three types of materials allow for the transfer of oxygen and moisture required to metabolize the wound healing physiology. Chitosan also has anti-microbial properties, which is crucial for a material covering open wounds and is useful in providing hemostasis due to its interaction with blood. Positive charges along the backbone of chitosan cause it to interact electrostatically with negatively charged blood cells, thus creating a sticky interface between chitosan foam and the wound. However, this initial electrostatic interaction is often overwhelmed by voluminous bloodflow in critical injuries, rendering the unmodified chitosan ineffective.

Cellulosics include, for example, hydroxyetyhl cellulose, hydroxypropyl cellulose, methyl cellulose, hydroxypropyl methyl cellulose, hydroxyethyl methyl cellulose, and other similar compounds. Chitosans include, for example, the following chitosan salts: chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof. Alginates include, for example, sodium alginate, potassium alginate, magnesium alginate, calcium alginate, aluminum alginate, and other known alginates. In an example, the polymeric component of the foam comprises mixtures of different types of hydrophobically modified polysaccharides, e.g., cellulusics and chitosans. In other embodiments different types of the same class of hydrophobically modified polysaccharide may be utilized, e.g. two alginates.

Figure 6:
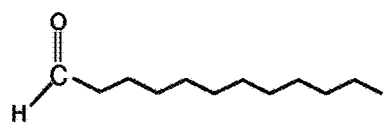
FIG. 6 is a chemical representation of three exemplary molecules that can be utilized as hydrophobic substitutents for the modification of hm-chitosan.
Figure 6:
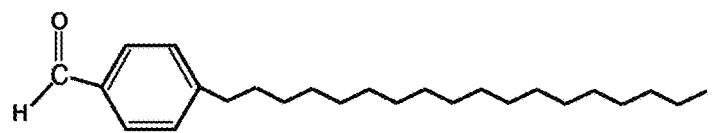
Figure 6:
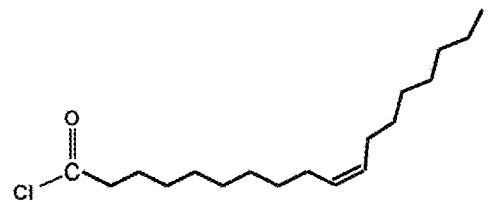
Figure 7:
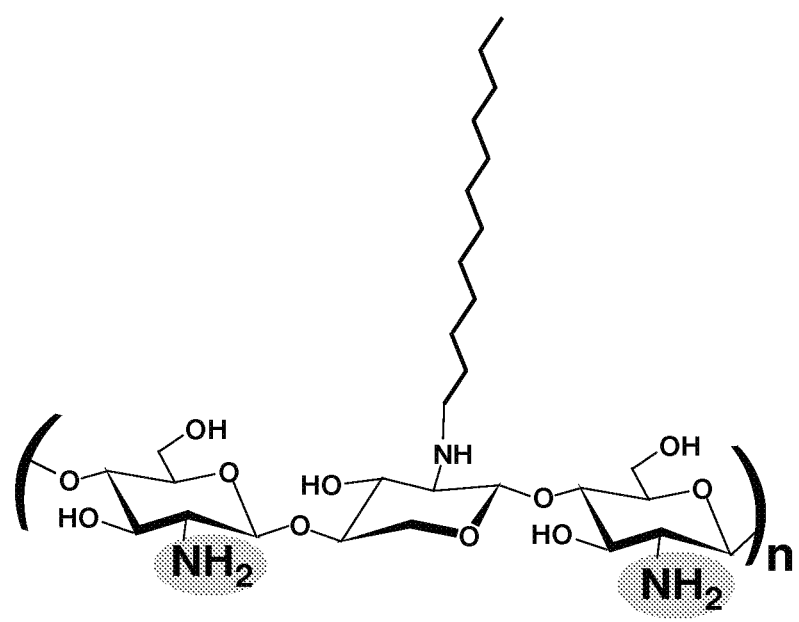
FIG. 7 is a chemical representation of hm-chitosan with a modification added by the reaction with dodecyl aldehyde.
Figure 8:
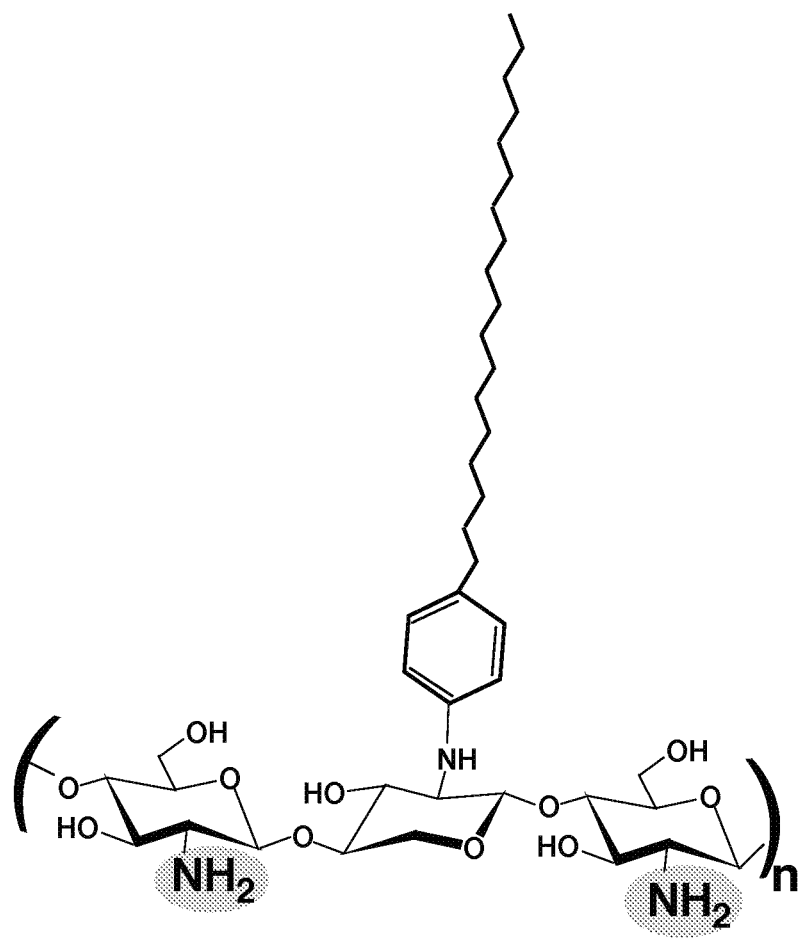
FIG. 8 is a chemical representation of hm-chitosan with a modification added by the reaction with 4-octadecyl benzaldehyde.
Figure 9:
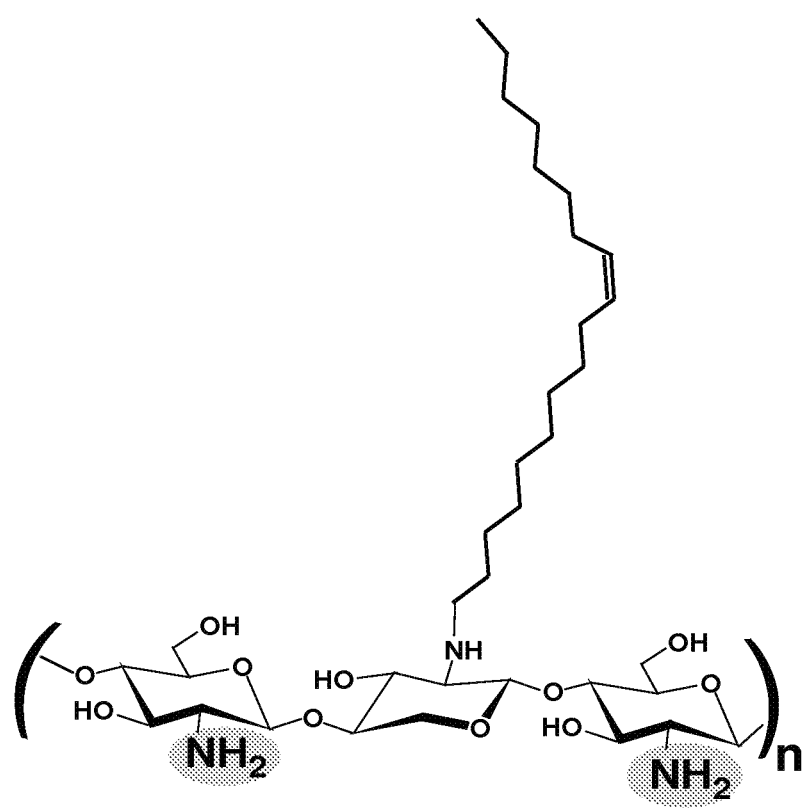
FIG. 9 is a chemical representation of hm-chitosan with a modification added by the reaction with cis-oleoyl chloride.

A hydrophobic substituent comprising a hydrocarbon group having from preferably about 8 to about 24 carbon atoms is attached to the backbone of the at least one polysaccharide. In an example, the hydrocarbon group comprises an alkyl or arylalkyl group. As used herein, the term "arylalkyl group" means a group containing both aromatic and aliphatic structures. It is contemplated that various substitutions may be utilized including, for example, those disclosed in United Stats Patent Application Publication Numbers 2008/0254104 and 2009/006284, which are hereby incorporated by reference in their entirety. FIG. 6 shows three different compounds that can be utilized for modifying hm-chitosan as described above. Once chitosan has been hydrophobically modified, its structure changes as shown on FIGS. 7 through 9.

Some examples of various linear alkanes that can be used as substituents for the hydrophobically modified polymer include:

| Number of C atoms | Formula | Common name | Synonyms |
|---|---|---|---|
| 8 | $C_8H_{18}$ | n-Octane | dibutyl; octyl hydride |
| 9 | $C_9H_{20}$ | n-Nonane | nonyl hydride; Shellsol 140 |
| 10 | $C_{10}H_{22}$ | n-Decane | decyl hydride |
| 11 | $C_{11}H_{24}$ | n-Undecane | hendecane |
| 12 | $C_{12}H_{26}$ | n-Dodecane | adakane 12; bihexyl; dihexyl; duodecane |
| 13 | $C_{13}H_{28}$ | n-Tridecane | |
| 14 | $C_{14}H_{30}$ | n-Tetradecane | |
| 15 | $C_{15}H_{32}$ | n-Pentadecane | |
| 16 | $C_{16}H_{34}$ | n-Hexadecane | cetane |
| 17 | $C_{17}H_{36}$ | n-Heptadecane | |
| 18 | $C_{18}H_{38}$ | n-Octadecane | |
| 19 | $C_{19}H_{40}$ | n-Nonadecane | |
| 20 | $C_{20}H_{42}$ | n-Eicosane | didecyl |
| 21 | $C_{21}H_{44}$ | n-Heneicosane | |
| 22 | $C_{22}H_{46}$ | n-Docosane | |
| 23 | $C_{23}H_{48}$ | n-Tricosane | |
| 24 | $C_{24}H_{50}$ | n-Tetracosane | tetrakosane |

Some cyclic compounds that can be utilized as substituents include:
Cyclic compounds can be categorized:

| | |
|---|---|
| Alicyclic Compound Cycloalkane Cycloalkene | An organic compound that is both aliphatic and cyclic with or without side chains attached. Typically include one or more all-carbon rings (may be saturated or unsaturated), but NO aromatic character. |
| Aromatic hydrocarbon Polycyclic aromatic hydrocarbon | See above and below |
| Heterocyclic compound | Organic compounds with a ring structure containing atoms in addition to carbon, such as nitrogen, oxygen, sulfur, chloride as part of the ring. May be simple aromatic rings or non-aromatic rings. Some examples are Pyridine (C5H5N), Pyrimidine (C4H4N2) and Dioxane (C4H8O2). |
| Macrocycle | See below. |

Polycyclic Compounds—polycyclic compound is a cyclic compound with more than one hydrocarbon loop or ring structures (Benzene rings). The term generally includes all polycyclic aromatic compounds, including the polycyclic aromatic hydrocarbons, the heterocyclic aromatic compounds containing sulfur, nitrogen, oxygen, or another non-carbon atoms, and substituted derivatives of these. The following is a list of some known polycyclic compounds.

| Polycyclic Compounds | Sub-Types | Example Compounds |
|---|---|---|
| Bridged Compound -- compounds which contain interlocking rings | Bicyclo compound | adamantane amantadine biperiden memantine methenamine rimantadine |
| Macrocyclic Compounds -- any molecule containing a ring of seven, fifteen, or any arbitrarily large number of atoms | Calixarene Crown Compounds Cyclodextrins Cycloparaffins Ethers, cyclic Lactams, macrocyclic Macrolides Peptides, cyclic Tetrapyrroles Trichothecenes | |
| Polycyclic Hydrocarbons, Aromatic | Acenaphthenes Anthracenes Azulenes Benz(a)anthracenes Benzocycloheptenes Fluorenes Indenes Naphthalenes Phenalenes Phenanthrenes Pyrenes Spiro Compounds | |
| Steroids | Androstanes Bile Acids and Salts Bufanolides Cardanolides Cholanes Choestanes Cyclosteroids Estranes Gonanes Homosteroids Hydroxysteroids Ketosteroids Norsteroids Prenanes Secosteroids Spirostans Steroids, Brominated Steroids, Chlorinated Steroids, Fluorinated Steroids, Heterocyclic | |

Figure 3A:
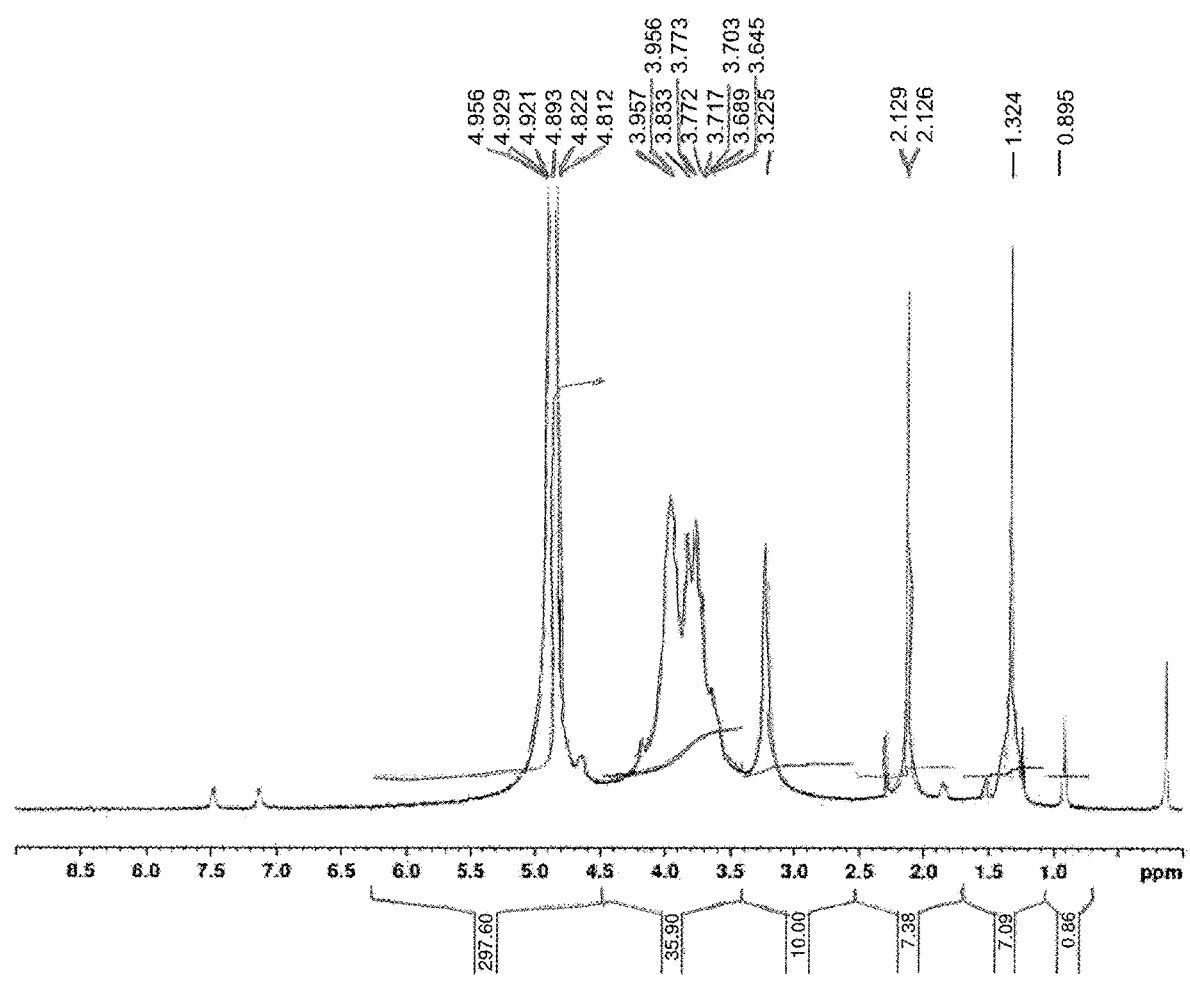
FIG. 3a is an H-NMR spectrum of hydrophobically-modified chitosan (4-octadecyl benzene, 2.5% of available amines).

Procedures for hydrophobically modifying the above mentioned polysaccharides are as follows:

1) Alginates can be hydrophobically modified by exchanging their positively charged counter-ions (e.g. $Na^+$) with tertiary-butyl ammonium ($TBA^+$) ions using a sulfonated ion exchange resin. The resulting TBA-alginate can be dissolved in dimethylsulfoxide (DMSO) where reaction between alkyl (or aryl) bromides and the carboxylate groups along the alginate backbone. 2) Cellulosics can be hydrophobically-modified by first treating the cellulosic material with a large excess highly basic aqueous solution (e.g. 20 wt % sodium hydroxide in water). The alkali cellulose is then removed from solution and vigorously mixed with an emulsifying solution (a typical emulsifier is oleic acid) containing the reactant, which is an alkyl (or aryl) halide (e.g. dodecyl bromide). 3) Chitosans can be hydrophobically-modified by reaction of alkyl (or aryl) aldehydes with primary amine groups along the chitosan backbone in a 50/50 (v/v) % of aqueous 0.2 M acetic acid and ethanol. After reaction, the resulting Schiff bases, or imine groups, are reduced to stable secondary amines by dropwise addition of the reducing agent sodium cyanoborohydride. Additionally, fatty halides, such as oleoyl chlorides, may be reacted with primary amines along the chitosan backbone. In this case, chitosan is soaked in pyridine for one week and then residual pyridine is evaporated under reduced pressure. Next, the chitosan is soaked again in a mixture of pyridine:chloroform at a ratio of 2:1 for one day. The mixture is then cooled between −10° C. and −5° C. in an ice-salt bath. Subsequently, oleoyl chloride dissolved in chloroform is added dropwise to the mixture for 2 h. The mixture will then be stirred for 8 h at room temperature. A large amount of methanol or acetone can then be added to the mixture in order to precipitate the chitosan. The chitosan is then filtered out of the solution, washed several times with methanol, and finally dried under vacuum to obtain the final product. The level of modification to the chitosan can be dialed up or down based on the feed ratio of chitosan to oleoyl chloride. The H-NMR spectrum for hm-chitosan with 4-octadecyl (C18) benzene substitutions is shown in FIG. 3a.

Figure 3B:
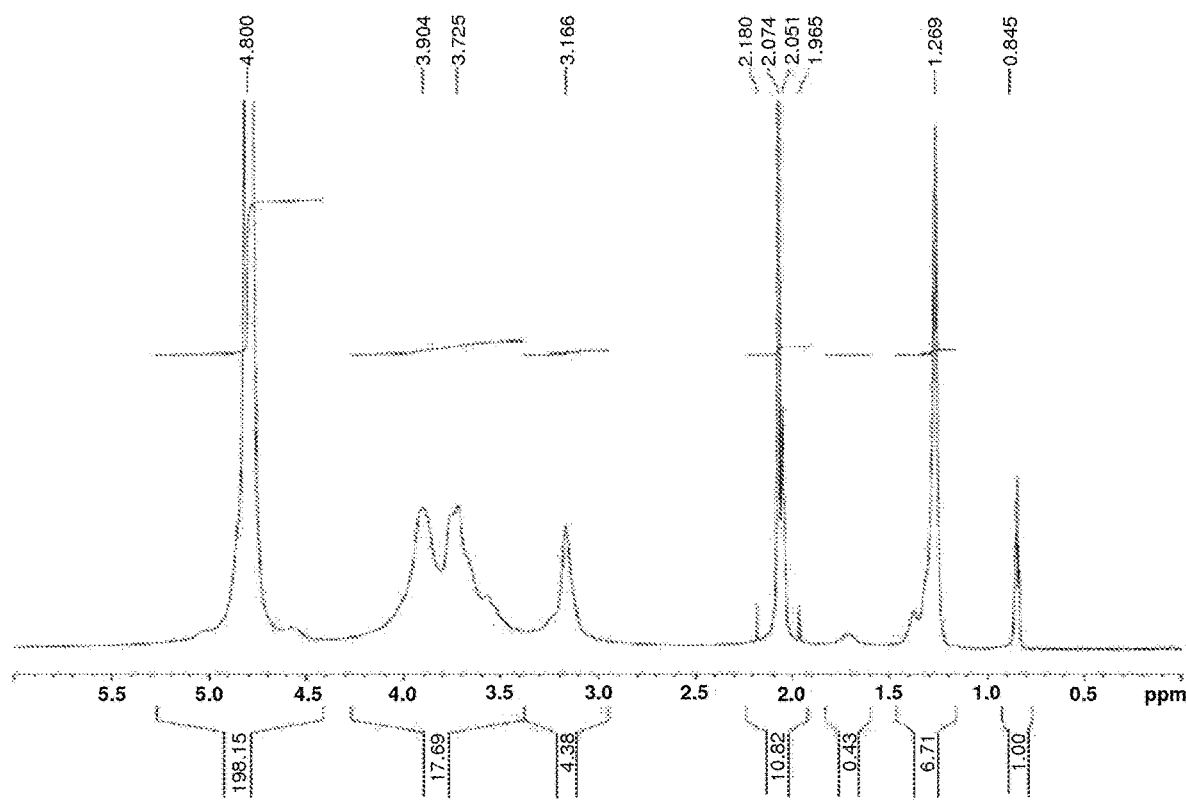
FIG. 3b is an H-NMR spectrum of hydrophobically-modified chitosan (n-dodecyl [C12] tails, 2.5% of available amines).

In one embodiment of the present hemostatic composition, the degree of substitution of the hydrophobic substituent on the polysaccharide is from about 1 to about 100 moles of the hydrophobic substituent per mole of the polysaccharide. In another embodiment, a hydrophobically modified chitosan is one in which 5 mol % of available amines along chitosan backbone are reacted with short aldehydes, e.g., C-12 aldehdydes, in 0.2 M Acetic or L-Lactic Acid. In another embodiment, more than one particular hydrophobic substituent is substituted onto the polysaccharide, provided that the total substitution level is substantially within the ranges set forth above. In a further preferred embodiment, the degree of substitution of the hydrophobic substituent on the polysaccharide is from about 40 to 65 moles of the hydrophobic substituent per mole of the polysaccharide. The level of hydrophobic modification, such an n-dodecyl modified chitosan can be determined preferably by H-NMR spectroscopy, as shown in FIG. 3b, or by FTIR spectroscopy.

In another preferred embodiment, the molecular weight of the polysaccharides comprising the tissue foam composition range from about 50,000 to about 1,500,000 grams per mole. In examples, the molecular weight of the polysaccharides comprising the foam ranges from about 50,000 to about 25,000 grams per mole. As used herein, the term "molecular weight" means weight average molecular weight. The preferred methods for determining average molecular weight of polysaccharides are low angle laser light scattering (LLS) and Size Exclusion Chromatography (SEC). In performing low angle LLS, a dilute solution of the polysaccharide, typically 2% or less, is placed in the path of a monochromatic laser. Light scattered from the sample hits the detector, which is positioned at a low angle relative to the laser source. Fluctuation in scattered light over time is correlated with the average molecular weight of the polysaccharide in solution. In performing SEC measurements, again a dilute solution of polysaccharide, typically 2% or less, is injected into a packed column. The polysaccharide is separated based on the size of the dissolved polysaccharide molecules and compared with a series of standards to derive the molecular weight.

In accordance with another embodiment of the invention, the hydrophobically modified polysaccharide foam material is mixed with a variety of water-soluble reagents that result in faster and more efficient healing of the wound. A first class of reagents that is mixed with the hydrophobically modified polysaccharide is comprised of those reagents that contribute to the hemostatic integrity of the clot form with blood cells and tissues. Such reagents include proteins involved in acceleration of the formation of fibrin networks, i.e., clots, such as for example human thrombin, bovine thrombin, recombinant thrombin, and any of these thrombins in combination with human fibrinogen. Other examples of the first class of reagents include fibrinogen, Factor VIIa, and Factor XIII. A second class of reagents that is mixed with the hydrophobically modified polysaccharide is comprised of anti bacterial compounds that prevent microbial infection such as ampicillin, penicillin, bactroban, bacitracin, mupirocin, neomycin, vancomycin, ponericin G1, norfloxacin and silver. It is contemplated that various combinations of the reagents described above can be utilized as components of the solution packaged in the apparatus for delivery to wounds.

In one embodiment of the present invention, an aqueous liquid solution of about 0.1% to about 2.0% by weight of hydrophobically modified chitosan is loaded into a pressurized canister, such as those used for aerosol applications, such as spray cans. As used in this context, the term about means from 0.15% to 2.5%. The pressure can be any pressure that can be contained within the canister. For typical aluminum canisters, the diameter of 66 mm×542 mm can be easy for a surgeon or medic to use. Canisters of these dimensions have a capacity of between about 385 ml to about 740 ml.

Figure 10:
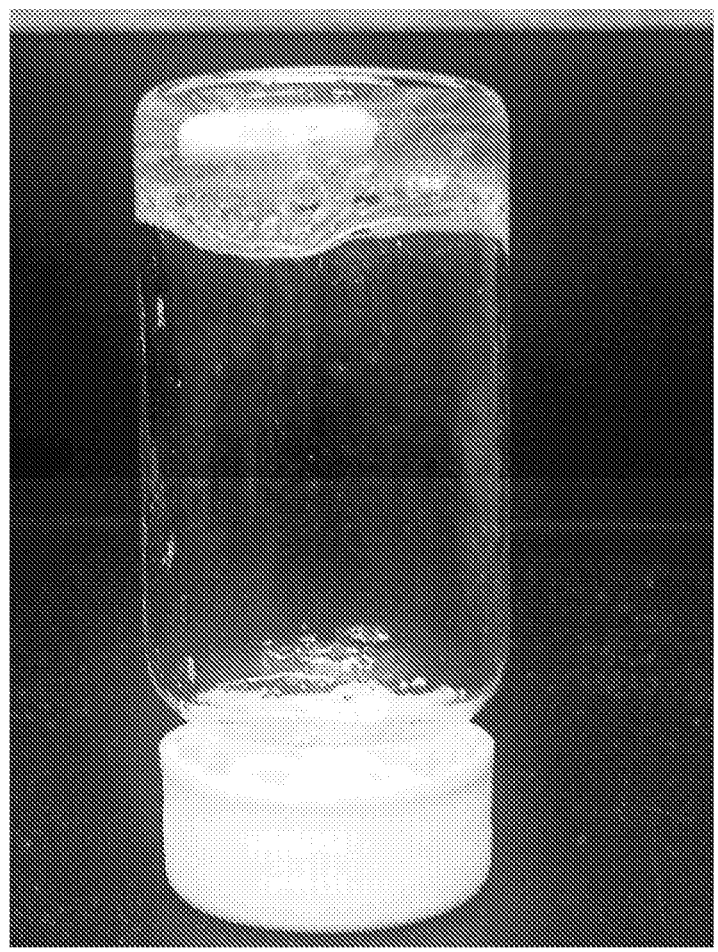
FIG. 10 is a picture of 4-octadecyl benzene modified chitosan.

In one preferred embodiment, the hm-chitosan has been modified by the addition of 4-octadecyl benzaldehyde. In this embodiment, a composition of between 0.1 wt % to 0.8 wt % of the hm-chitosan would be used in the foam canister. FIG. 10 shows a picture of 4-octadecyl benzene modified chitosan at 1.0 wt %. In another embodiment, where cis-oleoyl chloride is used, the concentration of the hm-chitosan can range from 0.2 wt % to 1.5 wt %.

The charging gas can be introduced at a pressure of between 21 and 180 pounds per square inch gauge "psig." However, stronger canisters, including those made of steel, can be pressurized from about 261 to 313 psig. After charging, a valve can seal the gas and hemostatic composition inside the canister, and the gas is allowed to equilibrate with the mixture. Valves can be obtained commercially, and for certain uses, polypropylene valves can be desirable.

The present hemostatic foam composition may also be useful in controlling intraoperative bleeding that has been exacerbated by genetic or acquired clotting defects or the use of anti-coagulation therapy. For example, if a patient receives anti-coagulation therapy following surgery and subsequently needs additional operations, the compositions of the present disclosure may be useful in counteracting any increased bleeding caused by the anti-coagulants. The compositions of the present disclosure may also be sterilized utilizing methods within the purview of those skilled in the art including, but not limited to, gamma radiation, ethylene oxide (EtO) sterilization, e-beam sterilization, aseptic treatments, and other methods recognized by a person having ordinary skill in the art.

The hemostatic foam is suitable for use in mammals. As used herein, the term "mammals" means any higher class of vertebrates that nourish their young with milk secreted by mammary glands, for example, humans, rabbits and monkeys.

In a further embodiment of the present invention, a method for treating compressible and non-compressible wounds is described. The method consists of applying a hydrophobically modified polysaccharide foam in a concentration of 0.1% to 2.0% by weight to a wound. In some embodiments of the present invention, the hydrophobically modified polysaccharide is hm-chitosan. In yet further embodiments, other reagents and elements as described above are applied with the hydrophobically modified polysaccharide, such as plasticizing agents, clotting agents, antimicrobials and antibacterials.

An aqueous liquid solution of about 0.2% to about 2.0% by weight of hydrophobically modified alginate (5 mol % of available carboxylic acid groups reacted with n-dodecyl bromide) is loaded into a pressurized canister in accordance with another embodiment of the present inventions. As used in this context, the term about means from 0.15% to 2.5%. For typical aluminum canisters, the diameter of 66 mm×542 mm can be easy for a surgeon or medic to use. Canisters of these dimensions have a capacity of between about 385 ml to about 740 ml.

The charging gas, propane, isopentane, isobutane, butane, propane, or some combination thereof, can be introduced at a pressure of between 21 and 180 pounds per square inch gauge "psig." However, stronger canisters, including those made of steel, can be pressurized from about 261 to 313 psig. After charging, a valve can seal the gas and hemostatic composition inside the canister, and the gas is allowed to equilibrate with the mixture. Valves can be obtained commercially, and for certain uses, polypropylene valves can be desirable.

Rheological Experiments: Steady shear rheological experiments were performed on a Rheometrics AR2000 stress-controlled rheometer. A cone-and-plate geometry of 40 mm diameter and 4° cone angle was used and samples were run at the physiological temperature of 37° C.

Figure 4:
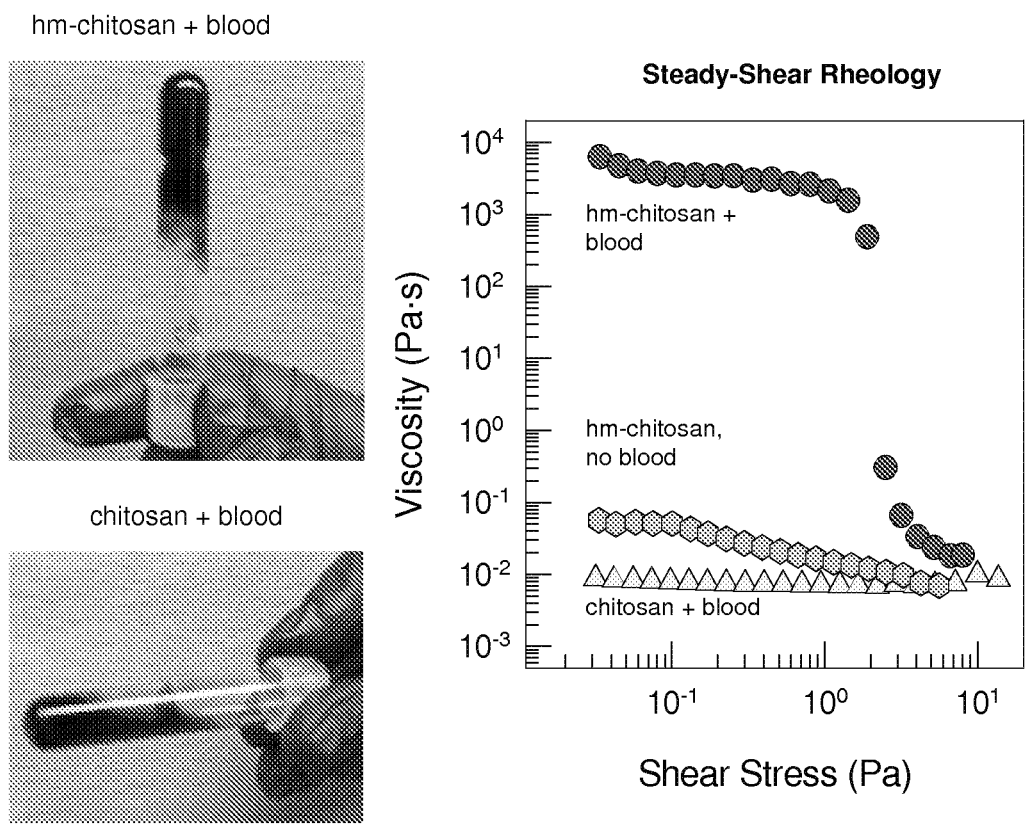
FIG. 4 is a picture showing a steady state rheology study of an hm-chitosan composition mixed with human heparized blood and a graph showing the viscosity over shear stress properties of chitosan, chitosan and blood, and hm-chitosan and blood.

Data on the same samples via steady-shear rheology are shown in FIG. 4, where the apparent viscosity is plotted as a function of shear stress. Here, we note that the chitosan/blood sample has a constant viscosity of about 0.01 Pa·s, which is about 4 times that of blood alone. A 0.25 wt % foam of hm-chitosan (4-octadecyl benzene, reacted with 2.5 mol % available amines) in water has a viscosity of about 0.07 Pa·s in the low-shear limit, indicating that the sample is slightly viscous but far from being a gel. In contrast, the sample of hm-chitosan foam/blood has a low-shear viscosity around 10,000 Pa·s, which is a million-fold higher than that of blood. Also, in this case, the steep drop in viscosity around a stress of 2 Pa is indicative of a yield stress, meaning that the sample hardly flows at stresses below this value. This accounts for the gel-like behavior seen in FIG. 4 where the sample holds its weight and does not flow down in the inverted tube.

Rat Injury Models. Surgical procedures were approved by the Institutional Animal Care and Use Committee (IACUC) at UMD. 15 fasted male Long-Evans rats (250-275 g, from Harlan Laboratories) were anesthetized (60 mg/kg ketamine and 7.5 mg/kg xylazine given IP) and allowed to breathe air. Animals were maintained under pathogen-free conditions in 12 h diurnal cycles, with water and food ad libitum. Animal rooms were kept at 21±3° C. with several changes of air per hour. All husbandry and animal procedures were in accordance with humane animal handling practices under the guidance of the Unit for Laboratory Animal Medicine at the UMD School of Medicine. At the end of each procedure, all animals were humanely sacrificed by ketamine administration.

Figure 5:
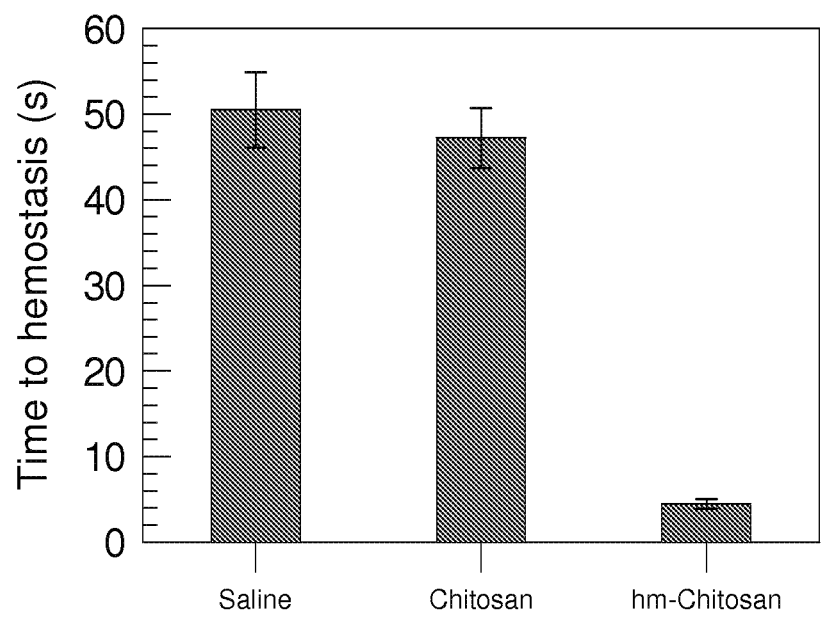
FIG. 5 is a bar graph comparing the time-to-hemostasis for hm-chitosan foam application in the rat femoral vein injury model and use of saline and regular unmodified chitosan.

Using a scalpel, the femoral vein was transected and allowed to bleed for 30 seconds, after a unilateral groin incision was made over the femoral canal. Exposure and isolation of at least 1 cm of the femoral vein was performed. 1 mL of hm-chitosan foam was dispensed onto the injury via Bag-On-Valve dispensing system ($N_2$ propellant) after wiping away excess blood from the site of injury via cotton gauze. Bleeding time was measured via stopwatch, with the start time corresponding to the application of sample and the end time corresponding to visual observation of halted blood flow. Test materials studied were (1) saline buffer, (2) 0.5 wt % chitosan solution and (3) 0.5 wt % hm-chitosan solution (4-octadecyl benzene, reacted with 2.5 mol % available amines), and the results are shown in FIG. 5.

Results—In vivo. The ability of hm-chitosan to gel blood is reminiscent of the natural clotting action of fibrin sealants. Therefore, it is pertinent to examine whether, like fibrin, hm-chitosan can also serve as a hemostatic sealant for bleeding injuries. To investigate this aspect, we conducted tests with animal injury models. First, we evaluated an injury in a small animal, and in this case, we tested an hm-chitosan foam as the hemostatic agent. Femoral vein injuries were created in Long-Evans adult rats (n=5 per sample) via scalpel. We then applied a given test foam to the injury via Bag-On-Valve dispensing system and measured the time to hemostasis, i.e., for the bleeding to cease (FIG. 5). First, 1 mL of a saline control was applied and in this case, hemostasis was achieved in 50±4 s (hemostasis here results from the rat's own blood coagulation cascade). Next, we applied 1 mL of a 0.5 wt % native chitosan solution and it showed a similar time to hemostasis of 47±3 sec. Finally, 1 mL of a 0.5 wt % hm-chitosan solution was applied, and in this case, hemostasis was attained in 3.8±0.6 sec—this is a 90% reduction compared to the controls. The hm-chitosan was also able to control bleeding from a minor injury model in a larger animal (porcine femoral vein injury) in a comparable period of time (5.6±0.7 s).

What is claimed is:

1. A method for treating a cavity wound including a non-compressible hemorrhage, comprising applying a hydrophobically-modified chitosan composition to a cavity wound including a non-compressible hemorrhage, wherein:
   the hydrophobically-modified chitosan composition does not comprise proteins involved in the accelerated formation of fibrin networks, and the composition comprises a foaming agent to foam and expand in the cavity and effect hemostasis with the hydrophobically modified chitosan; the hydrophobically-modified chitosan comprising hydrophobic substituents having from 8 to 24 carbon atoms so as to form a gel-like hemostatic network.

2. The method of claim 1, wherein the foaming agent is selected from sodium lauryl sulfate and sodium oleate.

3. The method of claim 1, wherein the composition further comprises one or more plasticizers selected from glycerol, glycerophosphate, polyethylene glycol, polyethylene oxide, tripolyphosphate, polycaprolactone, polyurethane, and silicone.

4. The method of claim 3, wherein hydropobically modified chitosan composition has a ratio of chitosan:plasticizer of 80:20 by weight.

5. The method of claim 1, wherein the hydrophobic substituents are alkanes.

6. The method of claim 1, wherein the hydrophobically modified chitosan has a concentration of 0.1% to 2.0% by weight.

7. The method of claim 1, wherein the hydrophobic modification of the chitosan is of 1 to 100 moles of a hydrophobic substituent per 1 mole of Chitosan.

8. The method of claim 1, wherein the hydrophobically modified composition further comprises one or more antibacterial compounds selected from ampicillin, penicillin, bactroban, bacitracin, mupirocin, neomycin, vanomycin, ponericin G1, norfloxacin, and silver.

* * * * *